United States Patent [19]

Kölling et al.

[11] 4,246,260
[45] Jan. 20, 1981

[54] SUBSTITUTED OMICRON-PHENYLENEDIAMINE DERIVATIVES, PROCESS FOR THEIR PREPARATION AND THEIR USE AS MEDICAMENTS

[75] Inventors: Heinrich Kölling, Haan; Ekkehard Niemers, Wuppertal; Hartmund Wollweber, Wuppertal; Herbert Thomas, Wuppertal, all of Fed. Rep. of Germany

[73] Assignee: Bayer Aktiengesellschaft, Leverkusen, Fed. Rep. of Germany

[21] Appl. No.: 21,869

[22] Filed: Mar. 19, 1979

Related U.S. Application Data

[63] Continuation of Ser. No. 845,517, Oct. 26, 1977, abandoned.

[30] Foreign Application Priority Data

Nov. 11, 1976 [DE] Fed. Rep. of Germany ....... 2651467

[51] Int. Cl.[3] .................. A61K 31/325; C07C 125/06
[52] U.S. Cl. .................................... 424/228; 424/244; 424/250; 424/267; 424/274; 424/286; 544/159; 544/162; 544/163; 544/165; 544/402; 546/246; 260/326.47; 260/397.6; 260/465 E; 560/9; 560/13; 560/25; 560/26
[58] Field of Search ........................ 560/25, 9, 13, 26; 260/397.6, 326.47, 465 B; 424/228, 286, 244, 250, 267, 274; 544/159, 162, 163, 165, 402; 546/246

[56] References Cited

U.S. PATENT DOCUMENTS

| | | | |
|---|---|---|---|
| 3,869,503 | 3/1975 | Widdig et al. | 560/25 |
| 3,993,682 | 11/1976 | Kolling et al. | 560/25 |
| 4,024,176 | 5/1977 | Kolling et al. | 560/25 |

*Primary Examiner*—John D. Randolph
*Attorney, Agent, or Firm*—Sprung, Felfe, Horn, Lynch & Kramer

[57] ABSTRACT

The invention relates to new substituted o-phenylenediamine derivatives of the general formula

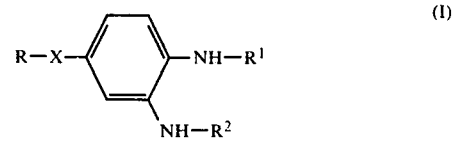

(I)

in which
R represents optionally substituted alkyl, optionally substituted alkenyl or optionally substituted alkinyl,
X represents O, S, SO or $SO_2$ and
$R^1$ and $R^2$ are different from one another and individually represent

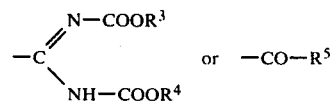

in which
$R^3$ and $R^4$ are identical or different and represent alkyl and
$R^5$ represents hydrogen, optionally substituted alkyl or optionally substituted alkoxy, and salts thereof.

Also included in the invention are (1) methods for preparing the above-described compounds, (2) compositions containing the above-described compounds and (3) methods for the treatment of helminthiasis.

27 Claims, No Drawings

SUBSTITUTED OMICRON-PHENYLENEDIAMINE DERIVATIVES, PROCESS FOR THEIR PREPARATION AND THEIR USE AS MEDICAMENTS

This s a continuation of application Ser. No. 845,517 filed Oct. 26, 1977, now abandoned.

The present invention relates to new substituted o-phenylenediamine derivatives, processes for their preparation and their use as medicaments, in particular as anthelmintics.

It has already been disclosed that phenylguanidines of the general formula

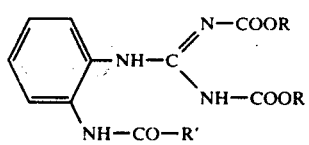

in which

R denotes lower alkyl and

R' denotes both lower alkyl and hydrogen, have anthelmintic actions (for this, see German Offenlegungsschrift (German Published Specification) No. 2,117,293).

According to the present invention, there are provided substituted o-phenylenediamine derivatives of the formula

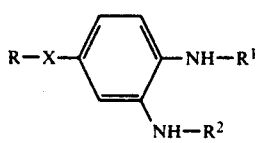

(I)

in which

R represents optionally substituted alkyl, optionally substituted alkenyl or optionally substituted alkinyl, X represents O, S, SO or $SO_2$ and $R^1$ and $R^2$ are different from one another and individually represent

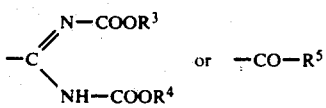

in which $R^3$ and $R^4$ are identical or different and represent alkyl and $R^5$ represents hydrogen, optionally substituted alkyl or optionally substituted alkoxy, and salts thereof.

The compounds of the invention (i.e. the compounds of the formula I and their salts) exhibit a very good anthelmintic action. Moreover, the anthelmintic action of the compounds of the invention is substantially more pronounced than that of the substituted known phenylguanidines referred to previously. Consequently of the compounds of the invention which are salts, those which are pharmaceutically acceptable are most important and preferred.

It has been found that the compounds of the invention are obtained when phenylamino compounds of the formula

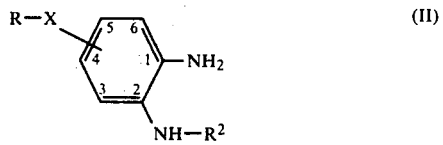

(II)

in which

X, R and $R^2$ have the meaning indicated above and in which

X can be linked to position 4 or position 5 of the substituted 1-amino-phenyl group of the formula (II), are reacted with isothioureas of the formula

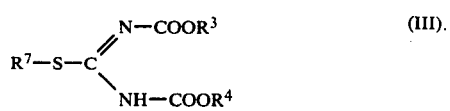

(III).

in which $R^3$ and $R^4$ have the meaning indicated above and $R^7$ represents alkyl with 1-4 carbon atoms, by methods which are in themselves known in the presence of a diluent and optionally in the presence of an acid.

In addition, it has also been found that the compound of the formula I, or their salts are obtained when compounds of the formula

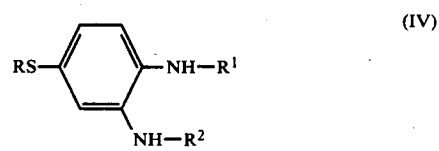

(IV)

in which

R, $R^1$ and $R^2$ have the meaning indicated above, are treated with the corresponding amount of an oxidising agent.

In the case where $R^1$ represents

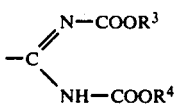

and $R^3$ and $R^4$ denote two non-identical alkyl groups, the compounds of the formula (I) according to the invention can exist in tautomeric forms, as the following example is intended to show:

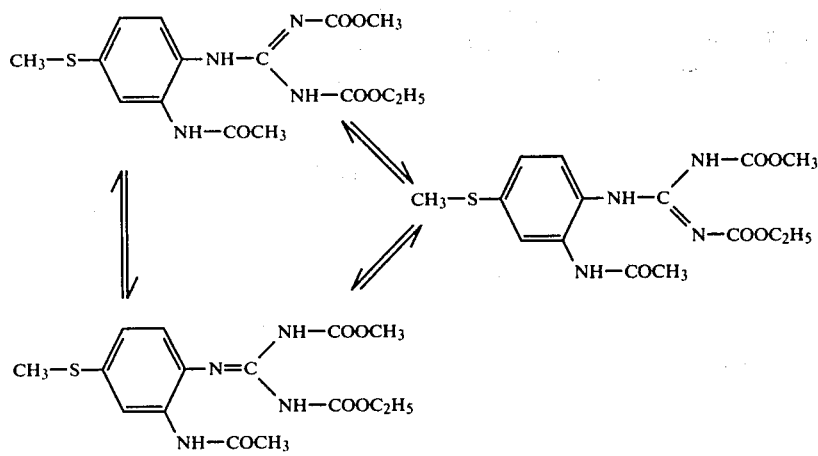

For reasons for uninformity, in the Application text the particular structural formulae are formulated in the same way in all cases. However, these formulae are to be construed as including all tautomeric forms of the compounds.

If N,N'-bis-methoxycarbonyl-S-methyl-isothiourea and 1-amino-2-acetamido-5-methoxy-benzene are used as the starting materials, the course of the reaction can be represented by the following equation:

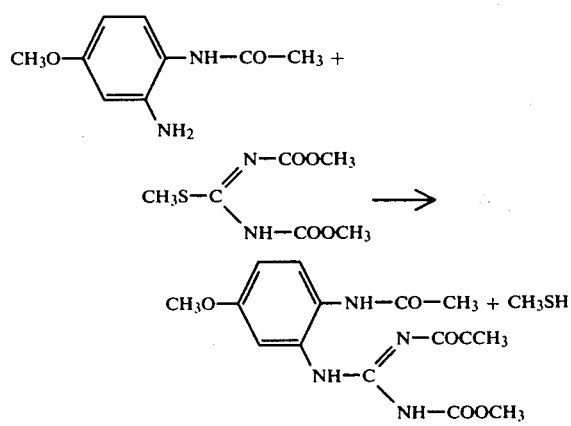

If N-(2-formylamino-4-propylthio-phenyl)-N',N''-bis-methoxycarbonyl-guanidine and hydrogen peroxide are used as the starting materials for the reaction of compounds of the formula (V) with oxidising agents, the course of the reaction can be represented by the following equation:

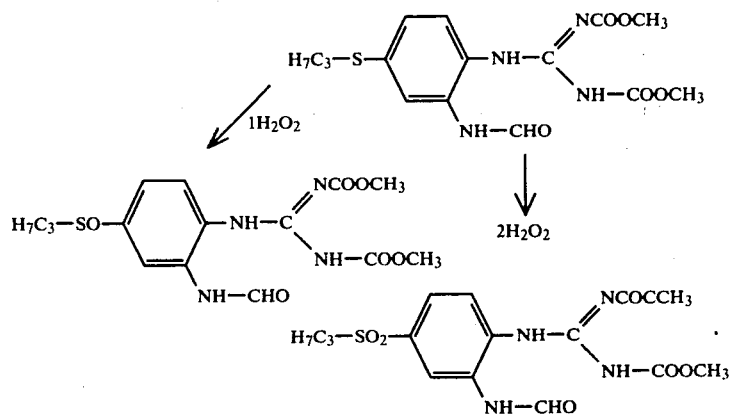

Preferred optionally substituted alkyl groups for the radicals R and $R^5$ include straight-chain or branched alkyl groups with 1 to 6, in particular 1 to 4, carbon atoms. Examples which may be mentioned are optionally substituted methyl, ethyl, n- and i-propyl and n-, i-, and t-butyl.

Preferred optionally substituted alkenyl groups for the radical R include straight-chain or branched alkenyl groups with 2 to 6, in particular 2 to 4, carbon atoms. Examples which may be mentioned are optionally substituted ethenyl, propen-1-yl, propen-2-yl and buten-3-yl.

Preferred optionally substituted alkinyl groups for the radical R include straight-chain or branched alkinyl groups with 2 to 6, in particular 2 to 4, carbon atoms. Examples which may be mentioned are optionally substituted ethinyl, propin-1-yl, propin-3-yl and butin-3-yl.

Preferred alkyl groups for the radicals $R^3$ and $R^4$ include straight-chain or branched alkyl groups with 1 to 6, in particular 1 to 4, carbon atoms. Examples which may be mentioned are optionally substituted methyl, ethyl, n- and i-propyl and n-, i- and t-butyl.

Preferred alkoxy groups for the radical $R^5$ include straight-chain or branched alkoxy groups with preferably 1 to 6, in particular 1 to 4, carbon atoms. Examples which may be mentioned are optionally substituted methoxy, ethoxy, n- and i-propoxy and n-, i- and t-butoxy.

Suitable substituents for the optionally substituted alkyl, alkenyl and alkinyl radical R which may be mentioned are halogen, especially fluorine, chlorine and bromine, cyano, ($C_1$–$C_4$)-alkoxy and ($C_1$–$C_4$)-alkylthio.

Suitable substituents for the optionally substituted alkyl radical $R^5$ which may be mentioned are: ($C_1$–$C_6$)-alkoxy, halogen, ($C_1$–$C_4$)-alkylmercapto, cyano, and radicals of the formula

in which
  $R^6$ and $R^7$ can be identical or different and each represents hydrogen or a ($C_1$–$C_4$)-alkyl group which is optionally substituted by ($C_1$–$C_4$)-alkoxy, trifluoromethyl or cyano, or
in which
  the two radicals $R^6$ and $R^7$, together with the nitrogen atom to which they are attached form a 5-membered, 6-membered or 7-membered heterocyclic ring which can be interrupted by further hetero-atoms (such as N, O and S) and can be saturated or unsaturated.

Examples of individual substituted alkyl, alkenyl or alkinyl radicals R which may be mentioned are: chloropropyl, chlorobutyl, cyanoethyl, cyanopropyl, cyanobutyl, cyanohexyl, bromopropyl, bromobutyl, trifluoromethyl, trifluoroethyl, fluoropropyl, fluorobutyl, 3-chloropropen-2-yl, 2,3-dichloropropen-2-yl, 3-chloro-3-methyl-propen-2-yl, 2-methoxyethyl, 2-ethoxyethyl, 3-methoxypropyl, 2-methylmercaptoethyl, 2-ethylmercaptoethyl and 2-mercaptopropyl.

Examples of individual substituted alkyl radicals $R^5$ which may be mentioned are: methoxyethyl, ethoxyethyl, methylmercaptoethyl, ethylmercaptoethyl, methylmercaptopropyl, chloromethyl, chloroethyl, cyanomethyl and cyanoethyl.

Examples of radicals

which may be mentioned are: dimethylamino, diethylamino, dipropylamino, pyrrolidinyl, piperidinyl and hexamethyleneiminyl, and examples which may be mentioned for an interruption of the ring by a further hetero-atom such as N, O and S are morpholinyl, thiomorpholinyl, piperazinyl and N-methylpiperazinyl.

Examples of further individual substituted alkyl radicals $R^5$ which may be mentioned are: dimethylaminomethyl, dimethylaminoethyl, diethylaminomethyl, diethylaminoethyl, pyrrolidinomethyl, pyrrolidinoethyl, pyrrolidinopropyl, piperidinomethyl, piperidinoethyl, hexamethyleneiminomethyl, hexamethyleneiminoethyl, morpholinomethyl, morpholinoethyl, morpholinopropyl, thiomorpholinoethyl, piperazinomethyl, piperazinoethyl, N-methylpiperazinoethyl and the like.

The thioureas used as starting materials are defined by the formula (III) and are known.

Some of the substituted phenylamino compounds of the formula (II) used as starting materials are not yet known. However, they can be easily prepared analogously to processes known from the literature. Thus, for example, 1-amino-2-acetamido-4-propylthio-benzene is obtained by the following reaction sequence:

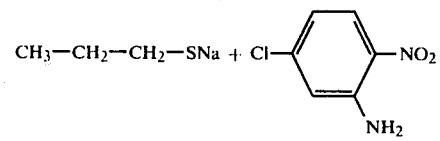

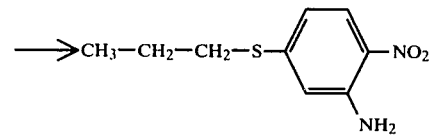

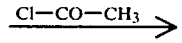

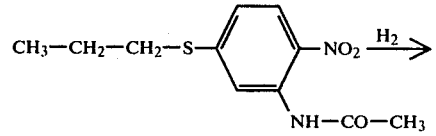

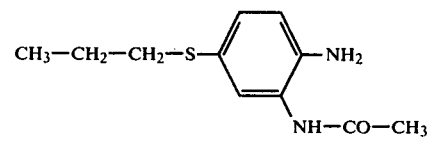

1-Amino-2-acetamido-5-butoxy-benzene is obtained, for example, according to the reaction scheme:

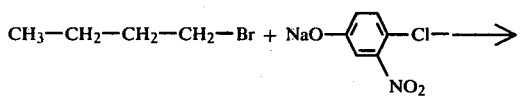

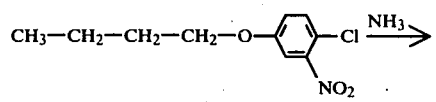

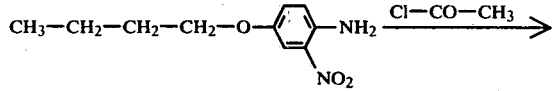

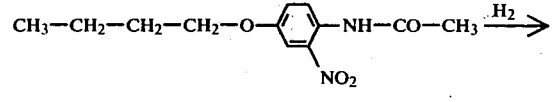

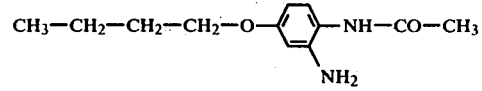

and 1-amino-2-β-piperidino-acetamido-4-propylthio-benzene is obtained, for example, according to the reaction sequence:

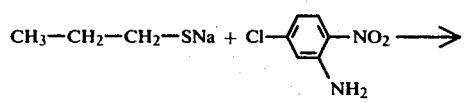

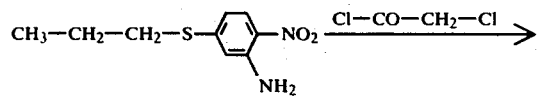

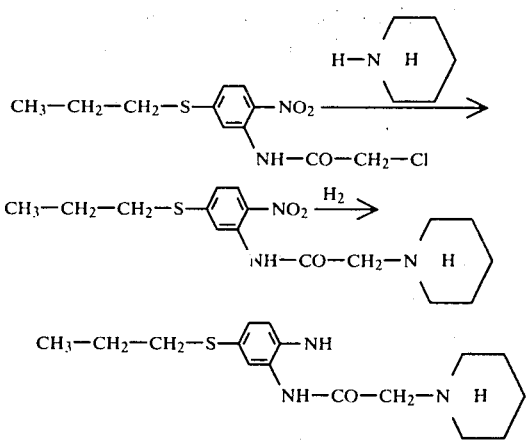

The 2-amino-4-substituted anilides can be prepared by the processes indicated in the following formula scheme, for example:

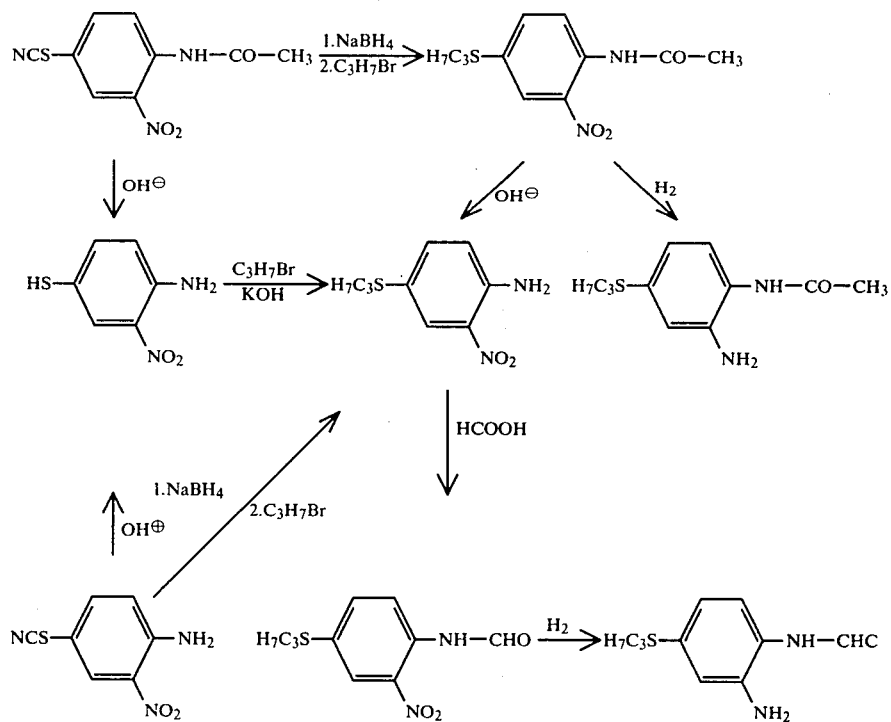

sulphuric acid, nitric acid, formic acid, acetic acid and p-toluenesulphonic acid.

The reaction temperatures can be varied within a wide range. In general, the reaction is carried out between about 0° and 120° C., preferably between about 0° and 80° C. In general, the reaction is carried out under normal pressure.

In general, molar amounts are employed when carrying out the reaction of compounds of the formula (II) with those of the formula (III).

In addition to hydrogen peroxide, the following may be mentioned as examples of oxidising agents which can be used for the oxidation of o-phenylenediamine derivatives of the formula (V): organic peracids, such as peracetic acid, performic acid, perbenzoic acid, m-chloroperbenzoic acid and monoperphthalic acid, inorganic peroxides, such as hydrogen peroxide, dissolved in water or dilute organic acids, inorganic oxidising agents, such as chromic acid, nitric acid, potassium permanganate, chlorine, bromine, halogen oxyacids, such as hypochlorous, chlorous, chloric or perchloric acid, tert-butyl hypochlorite, methyl hypochlorite or Diluents which can be used for the reaction of compounds of the formula (II) with isothioureas of the formula (III) include all inert polar organic solvents. These include, preferably, alcohols, preferably alkanols having up to six carbon atoms, such as methanol, ethanol, iso-propanol and their mixtures with water, ketones, such as acetone, methyl ethyl ketone (also mixed with water), but also ethers, such as dioxane or tetrahydrofurane or diethylether, diisopropyl ether.

In principle, the acids added as catalysts which promote the reaction can be chosen as desired from the range of known organic or inorganic acids. However, the easily accessible, industrially important representatives of these classes are advantageously used. Examples which may be mentioned are: hydrochloric acid, tert-butyl chromate, or organic N-halogeno compounds, such as N-chlorosuccinimide, N-bromosuccinimide and N-halogenosulphonic acid amides or N-halogenocarboxylic acid amides.

In general, the oxidation of compounds of the formula (IV) to the substances of the formula (I) is carried out in a diluent which is inert towards the reaction, such as, for example, acetic anhydride or acetic acid, at temperatures from about 0°–100° C., preferably at about 20° to 60° C.

By appropriate choice, which in itself is known from the literature, of the oxidising agents and the reaction conditions, the oxidation potential can be accordingly adjusted in each case, so that the oxidation reaction can be controlled to prepare the sulphoxides (compounds of the general formula (IV) in which Z represents SO), or the sulphones (compounds of the general formula (IV) in which Z represents SO₂).

The new compounds can be administered orally and, if they carry a basic centre, also, surprisingly, parenterally, the latter also being used in the form of their physiologically acceptable salts, such as, for example, hydrohalides, preferably hydrochlorides, sulphates, phosphates, nitrates, maleates, fumarates, acetates, methanesulphonates, naphthalenedisulphonates and others.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicylic, embonic, nicotinic, methanesulfonic, ethanesulfonic, hydroxyethanesulfonic, ethylenesulfonic, benzenesulfonic, halogenbenzenesulfonic, toluensulfonic, naphthalenesulfonic and sulfanilic acid; methionine, tryptophan, lysine and arginine.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds prepared according to the invention exhibit a surprisingly good and broad action against the following nematodes and cestodes:

1. Hookworms (for example Uncinaria stenocephala, Ancylostoma caninum and Bunostomum trigonocephalum)
2. Trichostrongylidae (for example Nippostrongylus muris, Haemonchus contortus, Trichostrongylus colubriformis and Ostertagia circumcincta)
3. Strongylidae (for example Oesophagostomum columbianum)
4. Rhabditidae (for example Strongyloides ratti)
5. Maw-worms (for example Ascaris suum, Toxocara canis and Toxascaris leonina)
6. Pin-worms (for example Aspiculuris tetraptera)
7. Heterakidae (for example Heterakis spumosa)
8. Whip-worms (for example Trichuris muris)
9. Filariae (for example Litomosoides carinii and Dipetalonema witei)
10. Cestodes (for example Hymenolepis nana, Taenia pisiformis and Echinococcus multilocularis)
11. Trematodes (for example Fasciola hepatica).

Their action was tested in animal experiments after oral and parenteral administration to test animals heavily infected with parasites. The doses used are tolerated very well by the test animals.

The new active compounds can be used as anthelmintics both in medicine.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily does of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes creams, spray (including aerosols), lotions, suspensions, solutions and emulsions of the active ingredient in aqueous or non-aqueous diluents, syrups, granules or powders.

The diluents to be used in pharmaceutical compositions (e.g. granulates) adapted to be formed into tablets, dragees, caspules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) distintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g.

cocoa oil and high esters [e.g. $C_{14}$-alcohol with $C_{16}$-fatty acid]) or mixtures of these diluents.

The pharmaceutical compositions which are ointments pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exlcusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium methahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granules), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 5 mg to 5 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent on in the form of a medicament according to the invention.

It is envisaged that these active compounds will be administered perorally, parenterally (for example intramuscularly, intraperitoneally or intravenously, or rectally, preferably orally. Parenteral, especially subcutaneous, administerion and dermal application is also practicable alternatives. The preferred compositions and medicaments are those adapted for oral administration.

In general, it has proved advantageous to administer amounts of about 0.1 to about 50 mg of the new compounds per kg of body weight per day in order to achieve effective results.

Nevertheless, it can at times be necessary to deviate from the amounts mentioned and in particular to do so as a function of the body weight of the test animal or the nature of the method of administration, but also depending on the species of animal and its individual behaviour towards the medicament or its type of formulation and the time or interval at which it is administered. Thus it can in some cases suffice to manage with less than the abovementioned minimum amount whilst in other cases the upper limit mentioned must be exceeded. Where larger amounts are administered it can be advisable to divide these into several individual administrations over the course of the day. The same dosage range is envisaged for administration in human medicine and in veterinary medicine. The general sense of the other comments made above also applies.

The anthelmintic action of the active compounds according to the invention is explained in more detail with the aid of the use examples which follow.

EXAMPLE A

Gastric and intestinal worm test/sheep

Sheep experimentally infected with Haemonchus contortus or Trichostrongylus coluoriformis were treated after the end of the pre-patency period of the parasites. The amount of active compound was administered orally as pure active compound in gelatine capsules.

The degree of action is determined by quantitatively counting the worm eggs excreted with the faeces before and after the treatment.

Complete cessation of the excretion of eggs after the treatment means that the worms have been expelled or have been damaged to the point that they can no longer produce eggs (effective dose).

The active compounds tested and effective doses (minimum effective dose) can be seen from the table which follows.

TABLE 1
(accompanying Example A)

| Active compound according to the invention | Minimum effective dose (reduction) >90% in mg/kg of body weight |
|---|---|
| $H_7C_3-O-\text{C}_6H_3(-NH-CO-CH_2-CH_3)(-NH-C(=N-COOCH_3)-NH-COOCH_3)$ | Haemonchus cont. 2.5 |
| $H_7C_3-O-\text{C}_6H_3(-NH-CO-CH_2-CH_2-CH_3)(-NH-C(=N-COOCH_3)-NH-COOCH_3)$ | Trichostrong. col. 2.5 |
| $H_9C_4-O-\text{C}_6H_3(-NH-CO-CH_2-CH_2-CH_3)(-NH-C(=N-COO-CH_3)-NH-COO-CH_3)$ | Trichostrong. col. 2.5 |
| $CH_3-CH_2-CH_2-S-\text{C}_6H_3(-NH-C(=N-COOCH_3)(NH-COOCH_3))(-NH-CO-CH_2-OCH_3)$ | Haemonchus cont. 1 |
| $C_3H_7S-\text{C}_6H_3(-NH-C(=N-COOCH_3)(NH-COOCH_3))(-NH-CO-C_2H_3)$ | Haemonchus cont. 0.5 |
| $C_3H_7S-\text{C}_6H_3(-NH-C(=N-COOCH_3)(NH-COOCH_3))(-NH-CO-C_3H_7)$ | Haemonchus cont. 0.5 |

Known preparation for comparison "Thiabendazole"

Thiabendazole structure (benzimidazole-thiazole)

| | Haemonchus cont. 50 Trichostrong. col. 25 |

Preparation examples

Example 1

$CH_3O-\text{C}_6H_3(-NH-CO-CH_3)(-NH-C(=N-COOCH_3)-NH-COOCH_3)$ 18 g (0.1 mol) of 1-amino-2-acetamido-5-methoxybenzene of melting point 151° C. are boiled, together with 20.6 g (0.1 mol) of N,N'-bis-methoxycarbonylisothiourea S-methyl ether and 2.6 g (0.015 mol) of p-toluenesulphonic acid, in 200 ml of absolute methanol for 3 hours, whilst stirring and under reflux.

The mixture is then filtered hot and, after cooling, the N-(2-acetamido-5-methoxy-phenyl)-N',N''-bis-methoxycarbonylguanidine which has crystallised out is filtered off, rinsed with ether and dried under a high vacuum, melting point 164° C., yield 20 g=59% of theory.

The yield can be increased by working up the mother liquor.

EXAMPLES 2 to 12

The compounds listed in the following Table were obtained analogously to Example 1.

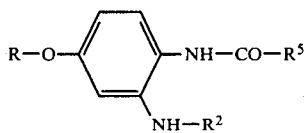

| | Starting materials | | | | Substances prepared according to the invention | | |
|---|---|---|---|---|---|---|---|
| Example No. | R | $R^5$ | $R^2$ | Melting point °C. | R | $R^5$ | $R^2$ | Melting point °C. |
| 2 | $CH_3$ | $C_2H_5$ | H | 118 | $CH_3$ | $C_2H_5$ | $-C\underset{NH-COOCH_3}{\overset{N-COOCH_3}{\diagup\!\!\!\diagdown}}$ | 167 |
| 3 | $CH_3$ | $C_3H_7(n)$ | H | 121 | $CH_3$ | $C_3H_7(n)$ | " | 165 |
| 4 | $C_2H_5$ | $CH_3$ | H | 146 | $C_2H_5$ | $CH_3$ | " | 173 |
| 5 | $C_2H_5$ | $C_2H_5$ | H | 134 | $C_2H_5$ | $C_2H_5$ | " | 168 |
| 6 | $C_2H_5$ | $C_3H_7(n)$ | H | 116 | $C_2H_5$ | $C_3H_7(n)$ | " | 164 |
| 7 | $C_3H_7(n)$ | $CH_3$ | H | 119 | $C_3H_7(n)$ | $CH_3$ | " | 153 |
| 8 | $C_3H_7(n)$ | $C_2H_5$ | H | 107 | $C_3H_7(n)$ | $C_2H_5$ | " | 144 |
| 9 | $C_3H_7(n)$ | $C_3H_7(n)$ | H | 133 | $C_3H_7(n)$ | $C_3H_7(n)$ | " | 132 |
| 10 | $C_4H_9(n)$ | $CH_3$ | H | 118 | $C_4H_9(n)$ | $CH_3$ | " | 143 |
| 11 | $C_4H_9(n)$ | $C_2H_5$ | H | 111 | $C_4H_9(n)$ | $C_2H_5$ | " | 152 |
| 12 | $C_4H_9(n)$ | $C_3H_7(n)$ | H | 121 | $C_4H_9(n)$ | $C_3H_7(n)$ | " | 136 |

EXAMPLE 13

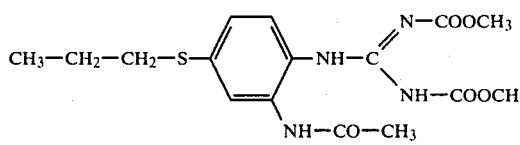

22.4 g (0.1 mol) of 2-amino-5-propylthio-acetanilide of melting point 98° C. are boiled, together with 20.6 g (0.1 mol) of N,N'-bis-methoxycarbonylisothiourea S-methyl ether and 2.6 g (0.015 mol) of p-toluenesulphonic acid, in 200 ml of absolute methanol for 3 hours, whilst stirring and under reflux. The mixture is then filtered hot and, after cooling, the N-(2-acetamido-4-propylthio-phenyl)-N',N''-bis-methoxycarbonyl-guanidine which has crystallised out is filtered off, rinsed with ether and dried under a high vaccum, melting point 149° C., yield 22 g=58% of theory. The yield can be further increased by working up the mother liquors.

EXAMPLES 14 to 99

The following compounds are obtained from N,N'-disubstituted isothiourea S-methyl ethers and 2-amino-5-substituted acylanilides by the method described in Example 13:

| | Starting materials $R-S-\underset{NH-COR^5}{\diagdown}-NH_2$ | | |
|---|---|---|---|
| Example No. | R | $R^5$ | Melting point (°C.) |
| 14 | $C_3H_7$ | $C_2H_5$ | 106 |
| 15 | $C_3H_7$ | $C_3H_7$ | 118 |
| 16 | $C_3H_7$ | $CH_2OCH_3$ | 68 |
| 17 | $C_3H_7$ | $OCH_3$ | |
| 18 | $C_3H_7$ | H | |
| 19 | $C_3H_7$ | H | |
| 20 | $C_3H_7$ | $C_4H_9$ | |
| 21 | $C_2H_5$ | H | |
| 22 | $C_2H_5$ | $C_3H_7$ | |
| 23 | $C_2H_5$ | $CH_2OCH_3$ | |
| 24 | $C_4H_9$ | H | |
| 25 | $C_4H_9$ | $C_3H_7$ | |
| 26 | $C_4H_9$ | $CH_2OCH_3$ | |
| 27 | $CH_2\!\!=\!\!CH\!\!=\!\!CH_2$ | H | |
| 28 | $CH_2\!\!=\!\!CH\!\!=\!\!CH_2$ | $C_2H_5$ | |
| 29 | $CH_2\!\!=\!\!CH\!\!=\!\!CH_2$ | $C_3H_7$ | |
| 30 | $HC\!\!\equiv\!\!C\!-\!CH_2$ | H | |
| 31 | $HC\!\!\equiv\!\!C\!-\!CH_2$ | $C_2H_5$ | |
| 32 | $HC\!\!\equiv\!\!C\!-\!CH_2$ | $C_3H_7$ | |
| 33 | $HC\!\!\equiv\!\!C\!-\!CH_2$ | $CH_2OCH_3$ | |
| 34 | $C_4H_9$ | $CH_3$ | |
| 35 | $C_4H_9$ | $C_2H_5$ | |
| 36 | $C_4H_9$ | $C_4H_9$ | |
| 37 | $C_5H_{11}$ | H | |
| 38 | $C_5H_{11}$ | $CH_3$ | |
| 39 | $C_5H_{11}$ | $CH_2OCH_3$ | |
| 40 | $H_3C\!-\!HC\!\!=\!\!CH\!-\!CH_2$ | H | |

| | | |
|---|---|---|
| 41 | H₃C—HC=CH—CH₂ | C₂H₅ |
| 42 | CH₂=C(CH₃)—CH₂ | H |
| 43 | CH₂=C(CH₃)—CH₂ | CH₂OCH₃ |
| 44 | CH₃O—CH₂—CH₂ | H |
| 45 | CH₃O—CH₂—CH₂ | CH₃ |
| 46 | CH₃O—CH₂—CH₂ | C₂H₅ |
| 47 | CH₃O—CH₂—CH₂ | C₃H₇ |
| 48 | CH₃O—CH₂—CH₂ | CH₂OCH₃ |
| 49 | CH₃O—CH₂—CH₂ | OCH₃ |
| 50 | CH₃S—CH₂—CH₂ | H |
| 51 | CH₃S—CH₂—CH₂ | CH₃ |
| 52 | CH₃S—CH₂—CH₂ | C₂H₅ |
| 53 | CH₂S—CH₂—CH₂ | CH₂—OCH₃ |
| 54 | NC—CH₂—CH₂ | H |
| 55 | NC—CH₂—CH₂ | CH₃ |
| 56 | NC—CH₂—CH₂ | C₂H₅ |
| 57 | NC—CH₂—CH₂ | CH₂—OCH₃ |
| 58 | NC—CH₂—CH₂—CH₂ | H |
| 59 | NC—CH₂—CH₂—CH₂ | CH₃ |
| 60 | NC—CH₂—CH₂—CH₂ | C₂H₅ |
| 61 | NC—CH₂—CH₂—CH₂ | C₃H₇ |
| 62 | NC—CH₂—CH₂—CH₂ | CH₂OCH₃ |
| 63 | CH₃O—CH₂—CH₂—CH₂ | H |
| 64 | CH₃O—CH₂—CH₂—CH₂ | CH₃ |
| 65 | CH₃O—CH₂—CH₂—CH₂ | C₂H₅ |
| 66 | CH₃O—CH₂—CH₂—CH₂ | C₃H₇ |
| 67 | CH₃O—CH₂—CH₂—CH₂ | CH₂OCH₃ |
| 68 | ClCH=CH—CH₂ | H |
| 69 | ClCH=CH—CH₂ | CH₃ |
| 70 | ClCH=CH—CH₂ | C₂H₅ |
| 71 | ClCH=CH—CH₂ | C₃H₇ |
| 72 | ClCH=CH—CH₂ | CH₂OCH₃ |
| 73 | Cl₂C=CHCH₂ | H |
| 74 | Cl₂C=CHCH₂ | CH₃ |
| 75 | Cl₂C=CHCH₂ | C₂H₅ |
| 76 | Cl₂C=CHCH₂ | C₂H₇ |
| 77 | Cl₂C=CHCH₂ | CH₂OCH₃ |
| 78 | ClCH=CCl—CH₂ | H |
| 79 | ClCH=CCl—CH₂ | CH₃ |
| 80 | ClCH=CCl—CH₂ | C₂H₅ |
| 81 | ClCH=CCl—CH₂ | C₃H₇ |
| 82 | ClCH=CCl—CH₂ | CH₂OCH₂ |
| 83 | H₃C—CCl=CH—CH₂ | H |
| 84 | H₃C—CCl=CH—CH₂ | CH₃ |
| 85 | H₃C—CCl=CH—CH₂ | C₂H₅ |
| 86 | H₃C—CCl=CH—CH₂ | C₃H₇ |
| 87 | H₃C—CCl=CH—CH₂ | CH₂OCH₃ |
| 88 | FHC=CH—CH₂ | H |
| 89 | FHC=CH—CH₂ | CH₃ |
| 90 | FHC=CH—CH₂ | C₂H₅ |
| 91 | FHC=CH—CH₂ | C₃H₇ |
| 92 | FHC=CH—CH₂ | CH₂OCH₃ |
| 93 | C₃H₇ | CH₂—N(CH₃)₂ |
| 94 | C₃H₇ | CH₂—N(C₂H₅)₂ |
| 95 | C₃H₇ | 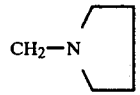 |
| 96 | C₃H₇ | 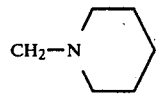 |
| 97 | C₃H₇ | 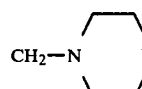 |
| 98 | C₃H₇ | 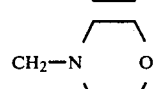 |
| 99 | C₃H₇ | 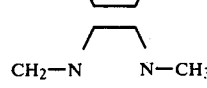 |

Substances prepared according to the invention

-continued $$R-S-\text{C}_6\text{H}_3(\text{NH}-\text{COR}^5)-\text{NH}-\text{C}(=\text{N}-\text{COOCH}_3)-\text{NH}-\text{COOR}^4$$

| Example No. | R | $R^5$ | $R^4$ | Melting point (°C.) |
|---|---|---|---|---|
| 14 | $C_3H_7$ | $C_2H_3$ | $CH_3$ | 148 |
| 15 | $C_3H_7$ | $C_3H_7$ | $CH_3$ | 153 |
| 16 | $C_3H_7$ | $CH_2OCH_3$ | $CH_3$ | 120 |
| 17 | $C_3H_7$ | $OCH_3$ | $CH_3$ | |
| 18 | $C_3H_7$ | H | $CH_3$ | 144 |
| 19 | $C_3H_7$ | H | $C_2H_3$ | |
| 20 | $C_3H_7$ | $C_4H_9$ | $CH_3$ | 139 |
| 21 | $C_2H_3$ | H | $CH_3$ | |
| 22 | $C_2H_5$ | $C_3H_7$ | $CH_3$ | |
| 23 | $C_2H_5$ | $CH_2OCH_3$ | $CH_3$ | |
| 24 | $C_4H_9$ | H | $CH_3$ | 144 |
| 25 | $C_4H_9$ | $C_3H_7$ | $CH_3$ | 134 |
| 26 | $C_4H_9$ | $CH_2OCH_3$ | $CH_3$ | 111 |
| 27 | $CH_2=CH-CH_2$ | H | $CH_3$ | |
| 28 | $CH_2=CH-CH_2C_2H_3$ | | $CH_3$ | |
| 29 | $CH_2=CH-CH_2C_3H_7$ | | $CH_3$ | |
| 30 | $HC\equiv C-CH_2$ | H | $CH_3$ | |
| 31 | $HC\equiv C-CH_2$ | $C_2H_3$ | $CH_3$ | |
| 32 | $HC\equiv C-CH_2$ | $C_3H_7$ | $CH_3$ | |
| 33 | $HC\equiv C-CH_2$ | $CH_2OCH_3$ | $CH_3$ | |
| 34 | $C_4H_9$ | $CH_3$ | $CH_3$ | 137 |
| 35 | $C_4H_9$ | $C_2H_5$ | $CH_3$ | 126 |
| 36 | $C_4H_9$ | $C_4H_9$ | $CH_3$ | 104 |
| 37 | $C_5H_{11}$ | H | $CH_3$ | 130 |
| 38 | $C_5H_{11}$ | $CH_3$ | $CH_3$ | 128 |
| 39 | $C_5H_{11}$ | $CH_2OCH_3$ | $CH_3$ | 86 |
| 40 | $CH_3-CH=CH-CH_2$ | H | $CH_3$ | |
| 41 | $CH_3-CH=CH-CH_2$ | | $CH_3$ | |
| 42 | $CH_2=C(CH_3)-C_2H_5$ | $CH_3$ | | |
| 43 | $CH_2=C(CH_3)-CH_2OCH_3$ | $CH_3$ | | |
| 44 | $CH_3-OCH_2-CH_2$ | H | $CH_3$ | |
| 45 | $CH_3-OCH_2-CH_2$ | $CH_3$ | $CH_3$ | |
| 46 | $CH_3-OCH_2-CH_2$ | $C_2H_5$ | $CH_3$ | |
| 47 | $CH_3-OCH_2-CH_2$ | $C_3H_7$ | $CH_3$ | |
| 48 | $CH_3-OCH_2-CH_2$ | $CH_2OCH_3$ | $CH_3$ | |
| 49 | $CH_3-OCH_2-CH_2$ | $OCH_3$ | $CH_3$ | |
| 50 | $CH_3S-CH_2-CH_2$ | H | $CH_3$ | |
| 51 | $CH_3S-CH_2-CH_2$ | $CH_3$ | $CH_3$ | |
| 52 | $CH_3S-CH_2-CH_2$ | $C_2H_5$ | $CH_3$ | |
| 53 | $CH_3S-CH_2-CH_2$ | $CH_2-OCH_3$ | $CH_3$ | |
| 54 | $NC-CH_2-CH_2$ | H | $CH_3$ | |
| 55 | $NC-CH_2-CH_2$ | $CH_3$ | $CH_3$ | |
| 56 | $NC-CH_2-CH_2$ | $C_2H_5$ | $CH_3$ | |
| 57 | $NC-CH_2-CH_2$ | $CH_2-OCH_3$ | $CH_3$ | |
| 58 | $NC-CH_2-CH_2-CH_2$ | H | $CH_3$ | |
| 59 | $NC-CH_2-CH_2-CH_2$ | $CH_3$ | $CH_3$ | |
| 60 | $NC-CH_2-CH_2-CH_2$ | $C_2H_5$ | $CH_3$ | |
| 61 | $NC-CH_2-CH_2-CH_2$ | $C_3H_7$ | $CH_3$ | |
| 62 | $NC-CH_2-CH_2-CH_2$ | $CH_2OCH_3$ | $CH_3$ | |
| 63 | $CH_3-CH_2-CH_2-CH_2$ | H | $CH_3$ | |
| 64 | $CH_3O-CH_2-CH_2-CH_2$ | $CH_3$ | $CH_3$ | |
| 65 | $CH_3O-CH_2-CH_2-CH_2$ | $C_2H_5$ | $CH_3$ | |
| 66 | $CH_3O-CH_2-CH_2-CH_2$ | $C_3H_7$ | $CH_3$ | |
| 67 | $CH_3O-CH_2-CH_2-CH_2$ | $CH_2OCH_3$ | $CH_3$ | |
| 68 | $ClCH=CH-CH_2$ | H | $CH_3$ | |
| 69 | $ClCH=CH-CH_2$ | $CH_3$ | $CH_3$ | |
| 70 | $ClCH=CH-CH_2$ | $C_2H_5$ | $CH_3$ | |
| 71 | $ClCH=CH-CH_2$ | $C_3H_7$ | $CH_3$ | |
| 72 | $ClCH=CH-CH_2$ | $CH_2OCH_3$ | $CH_3$ | |
| 73 | $Cl_2C=CH-CH_2$ | H | $CH_3$ | |
| 74 | $Cl_2C=CH-CH_2$ | $CH_3$ | $CH_3$ | |
| 75 | $Cl_2C=CH-CH_2$ | $C_2H_3$ | $CH_3$ | |
| 76 | $Cl_2C=CH-CH_2$ | $C_3H_7$ | $CH_3$ | |
| 77 | $Cl_2C=CH-CH_2$ | $CH_2OCH_3$ | $CH_3$ | |
| 78 | $ClCH=CCl-CH_2$ | H | $CH_3$ | |
| 79 | $ClCH=CCl-CH_2$ | $CH_3$ | $CH_3$ | |
| 80 | $ClCH=CCl-CH_2$ | $C_2H_3$ | $CH_3$ | |
| 81 | $ClCH=CCl-CH_2$ | $C_3H_7$ | $CH_3$ | |
| 82 | $ClCH=CCl-CH_2$ | $CH_2OCH_3$ | $CH_3$ | |
| 83 | $H_3C-CCl=CH-CH_2$ | H | $CH_3$ | |
| 84 | $H_3C-CCl=CH-CH_2$ | $CH_2$ | $CH_3$ | |
| 85 | $H_3C-CCl=CH-CH_2$ | $C_2H_3$ | $CH_3$ | |
| 86 | $H_3C-CCl=CH-CH_2$ | $C_3H_7$ | $CH_3$ | |
| 87 | $H_3C-CCl=CH_2$ | $CH_2OCH_3$ | $CH_3$ | |
| 88 | $FHC=CH-CH_2$ | H | $CH_3$ | |

-continued

| | | | |
|---|---|---|---|
| 89 | FHC=CH—CH$_2$ | CH$_3$ | CH$_3$ |
| 90 | FHC=CH—CH$_2$ | C$_2$H$_3$ | CH$_3$ |
| 91 | FHC=CH—CH$_2$ | C$_3$H$_7$ | CH$_3$ |
| 92 | FHC=CH—CH$_2$ | CH$_2$OCH$_3$ | CH$_3$ |
| 93 | C$_3$H$_7$ | CH$_2$—N(CH$_3$)$_2$ | CH$_3$ |
| 94 | C$_3$H$_7$ | CH$_2$—N(C$_2$H$_5$)$_2$ | CH$_3$ |
| 95 | C$_3$H$_7$ | CH$_2$—N⟨pyrrolidinyl⟩ | CH$_3$ |
| 96 | C$_3$H$_7$ | CH$_2$—N⟨piperidinyl⟩ | CH$_3$ |
| 97 | C$_3$H$_7$ | CH$_2$—N⟨hexahydroazepinyl⟩ | CH$_3$ |
| 98 | C$_3$H$_7$ | CH$_2$—N⟨morpholinyl⟩ | CH$_3$ 130 |
| 99 | C$_3$H$_7$ | CH$_2$—N⟨N-methylpiperazinyl⟩ | |

EXAMPLE 100

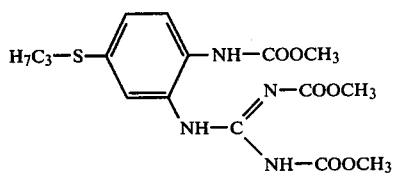

18.3 g (0.0815 mol) of 2-amino-4-propylthio-acetanilide are stirred, in 350 ml of methanol and 9.5 ml of glacial acetic acid, with 18.1 g (0.088 mol) of N,N'-bis-methoxycarbonyl-isothiourea S-methyl ether for 15 hours at room temperature. After cooling, the precipitate is filtered off, washed with ether and recrystallised from ethyl acetate. This gives 17 g of N-(2-acetylamino-5-propylthiophenyl)-N'-N''-bis-methoxycarbonyl-guanidine of melting point 138° C.

The 2-amino-4-propylthio-acetanilide (melting point 105° C.) used as the starting material is obtained by catalytic hydrogenation of 2-nitro-4-propylthio-acetanilide, melting point 76° C. The 2-Nitro-4-propylthio-acetanilide, is prepared by reacting 2-nitro-4-thiocyanatoacetanilide with propyl bromide in the presence of NaBH$_4$ in dimethylformamide as the solvent, or by acetylating 2-nitro-4-propylthio-aniline, melting point 41°–42° C., with acetic anhydride or acetyl chloride.

EXAMPLES 101 TO 184

The following compounds are obtained from N,N'-disubstituted isothiourea S-methyl ethers and 2-amino-4-substituted acylanilides by the method described in Example 13:

| | Starting materials | | | Substances prepared according to the invention | | | |
|---|---|---|---|---|---|---|---|
| Ex. No. | R | R$^5$ | Melting point (°C.) | R | R$^5$ | R$^4$ | Melting point (°C.) |
| 101 | C$_3$H$_7$ | C$_2$H$_5$ | 107 | C$_3$H$_7$ | C$_2$H$_5$ | CH$_3$ | 130 |
| 102 | C$_3$H$_7$ | C$_3$H$_7$ | 111 | C$_3$H$_7$ | C$_3$H$_7$ | CH$_3$ | 126 |
| 103 | C$_3$H$_7$ | CH$_2$OCH$_3$ | 54–55 | C$_3$H$_7$ | CH$_2$OCH$_3$ | CH$_3$ | 115–116 |
| 104 | C$_3$H$_7$ | OCH$_3$ | | C$_3$H$_7$ | OCH$_3$ | CH$_3$ | |
| 105 | C$_3$H$_7$ | H | 111–112 | C$_3$H$_7$ | H | CH$_3$ | 128–130 |
| 106 | C$_3$H$_7$ | H | | C$_3$H$_7$ | H | C$_2$H$_5$ | |
| 107 | C$_3$H$_7$ | C$_4$H$_9$ | 108–109 | C$_3$H$_7$ | C$_4$H$_9$ | CH$_3$ | 116–117 |
| 108 | C$_2$H$_5$ | H | | C$_2$H$_5$ | H | CH$_3$ | |
| 109 | C$_2$H$_5$ | C$_3$H$_7$ | | C$_2$H$_5$ | C$_3$H$_7$ | CH$_3$ | |
| 110 | C$_2$H$_5$ | CH$_2$OCH$_3$ | | C$_2$H$_5$ | CH$_2$OCH$_3$ | CH$_3$ | |
| 111 | C$_4$H$_9$ | H | 117–118 | C$_4$H$_9$ | H | CH$_3$ | 139 |
| 112 | C$_4$H$_9$ | C$_3$H$_7$ | | C$_4$H$_9$ | C$_3$H$_7$ | CH$_3$ | |
| 113 | C$_4$H$_9$ | CH$_2$OCH$_3$ | | C$_4$H$_9$ | CH$_2$OCH$_3$ | CH$_3$ | |
| 114 | CH$_2$=CH—CH$_2$ | H | | CH$_2$=CH—CH$_2$ | H | CH$_3$ | |
| 115 | CH$_2$=CH—CH$_2$ | C$_2$H$_5$ | | CH$_2$=CH—CH$_2$ | C$_2$H$_5$ | CH$_3$ | |

-continued

|  | Starting materials | | | Substances prepared according to the invention | | | |
|---|---|---|---|---|---|---|---|
|  | R–S–⟨⟩–NH–COR⁵ with NH₂ | | | R–S–⟨⟩–NH–COR⁵ / NH–C(=N–COOCH₃)(NH–COOR⁴) | | | |
| Ex. No. | R | $R^5$ | Melting point (°C.) | R | $R^5$ | $R^4$ | Melting point (°C.) |
| 116 | $CH_2=CH-CH_2$ | $C_3H_7$ |  | $CH_2=CH-CH_2$ | $C_3H_7$ | $CH_3$ |  |
| 117 | $HC\equiv C-CH_2$ | H |  | $HC\equiv C-CH_2$ | H | $CH_3$ |  |
| 118 | $HC\equiv C-CH_2$ | $C_2H_5$ |  | $HC\equiv C-CH_2$ | $C_2H_5$ | $CH_3$ |  |
| 119 | $HC\equiv C-CH_2$ | $C_3H_7$ |  | $HC\equiv C-CH_2$ | $C_3H_7$ | $CH_3$ |  |
| 120 | $HC\equiv C-CH_2$ | $CH_2OCH_3$ |  | $HC\equiv C-CH_2$ | $CH_2OCH_3$ | $CH_3$ |  |
| 121 | $C_4H_9$ | $C_2H_5$ | 109 | $C_4H_9$ | $C_2H_5$ | $CH_3$ | 120 |
| 122 | $C_4H_9$ | $CH_3$ | 114 | $C_4H_9$ | $CH_3$ | $CH_3$ | 144 |
| 123 | $H_3C-HC=CH-CH_2$ | H |  | $CH_3-CH=CH-CH_2$ | H | $CH_3$ |  |
| 124 | $H_3C-HC=CH-CH_2$ | $C_2H_5$ |  | $CH_3-CH=CH-CH_2C_2H_5$ |  | $CH_3$ |  |
| 125 | $CH_2=C(CH_3)-CH_2$ | H |  | $CH_2=C(CH_3)-CH_2$ | H | $CH_3$ |  |
| 126 | $CH_2=C(CH_3)$ | $CH_2OCH_3$ |  | $CH_2=C(CH_3)-CH_2CH_2$ | $OCH_3$ | $CH_3$ |  |
| 127 | $CH_3O-CH_2-CH_2$ | H |  | $CH_3-OCH_2-CH_2$ | H | $CH_3$ |  |
| 128 | $CH_3O-CH_2-CH_2$ | $CH_3$ |  | $CH_3-OCH_2-CH_2$ | $CH_3$ | $CH_3$ | 127-128 |
| 129 | $CH_3O-CH_2-CH_2$ | $C_2H_5$ |  | $CH_3-OCH_2-CH_2$ | $C_2H_5$ | $CH_3$ |  |
| 130 | $CH_3O-CH_2-CH_2$ | $C_3H_7$ |  | $CH_3-OCH_2-CH_2$ | $C_3H_7$ | $CH_3$ | 104-105 |
| 131 | $CH_3O-CH_2-CH_2$ | $CH_2OCH_3$ |  | $CH_3-OCH_2-CH_2$ | $CH_2OCH_3$ | $CH_3$ |  |
| 132 | $CH_3O-CH_2-CH_2$ | $OCH_3$ |  | $CH_3-OCH_2-CH_2$ | $OCH_3$ | $CH_3$ |  |
| 133 | $CH_3S-CH_2-CH_2$ | H |  | $CH_3S-CH_2-CH_2$ | H | $CH_3$ |  |
| 134 | $CH_3S-CH_2-CH_2$ | $CH_3$ |  | $CH_3S-CH_2-CH_2$ | $CH_3$ | $CH_3$ |  |
| 135 | $CH_3S-CH_2-CH_2$ | $C_2H_5$ |  | $CH_3S-CH_2-CH_2$ | $C_2H_5$ | $CH_3$ |  |
| 136 | $CH_3S-CH_2-CH_2$ | $CH_2-OCH_3$ |  | $CH_3S-CH_2-CH_2$ | $CH_2-OCH_3$ | $CH_3$ |  |
| 137 | $NC-CH_2-CH_2$ | H |  | $NC-CH_2-CH_2$ | H | $CH_3$ |  |
| 138 | $NC-CH_2-CH_2$ | $CH_3$ |  | $NC-CH_2-CH_2$ | $CH_3$ | $CH_3$ |  |
| 139 | $NC-CH_2-CH_2$ | $C_2H_5$ | 60-63 (decomposition) | $NC-CH_2-CH_2$ | $C_2H_5$ | $CH_3$ | 181 |
| 140 | $NC-CH_2-CH_2$ | $CH_2-OCH_3$ |  | $NC-CH_2-CH_2$ | $CH_2-OCH_3$ | $CH_3$ |  |
| 141 | $NC-CH_2-CH_2-CH_2$ | H |  | $NC-CH_2-CH_2-CH_2$ | H | $CH_3$ |  |
| 142 | $NC-CH_2-CH_2-CH_2$ | $CH_3$ |  | $NC-CH_2-CH_2-CH_2$ | $CH_3$ | $CH_3$ |  |
| 143 | $NC-CH_2-CH_2-CH_2$ | $C_2H_5$ |  | $NC-CH_2-CH_2-CH_2$ | $C_2H_5$ | $CH_3$ |  |
| 144 | $NC-CH_2-CH_2-CH_2$ | $C_3H_7$ |  | $NC-CH_2-CH_2-CH_2$ | $C_3H_7$ | $CH_3$ |  |
| 145 | $NC-CH_2-CH_2-CH_2$ | $CH_2OCH_3$ |  | $NC-CH_2-CH_2-CH_2$ | $CH_2OCH_3$ | $CH_3$ |  |
| 146 | $CH_3O-CH_2-CH_2-CH_2$ | H |  | $CH_3O-CH_2-CH_2-CH_2$ | H | $CH_3$ |  |
| 147 | $CH_3O-CH_2-CH_2-CH_2$ | $CH_3$ |  | $CH_3O-CH_2-CH_2-CH_2$ | $CH_3$ | $CH_3$ |  |
| 148 | $CH_3O-CH_2-CH_2-CH_2$ | $C_2H_5$ |  | $CH_3O-CH_2-CH_2-CH_2$ | $C_2H_5$ | $CH_3$ |  |
| 149 | $CH_3O-CH_2-CH_2-CH_2$ | $C_3H_7$ |  | $CH_3O-CH_2-CH_2-CH_2$ | $C_3H_7$ | $CH_3$ |  |
| 150 | $CH_3O-CH_2-CH_2-CH_2$ | $CH_2OCH_3$ |  | $CH_3O-CH_2-CH_2-CH_2$ | $CH_2OCH_3$ | $CH_3$ |  |
| 151 | $ClCH=CH-CH_2$ | H |  | $ClCH=CH-CH_2$ | H | $CH_3$ |  |
| 152 | $ClCH=CH-CH_2$ | $CH_3$ |  | $ClCH=CH-CH_2$ | $CH_3$ | $CH_3$ |  |
| 153 | $ClCH=CH-CH_2$ | $C_2H_5$ |  | $ClCH=CH-CH_2$ | $C_2H_5$ | $CH_3$ |  |
| 154 | $ClCH=CH-CH_2$ | $C_3H_7$ |  | $ClCH=CH-CH_2$ | $C_3H_7$ | $CH_3$ |  |
| 155 | $ClCH_2-CH_2-CH_2$ | $CH_3$ | 130-132 | $ClCH_2-CH_2-CH_2$ | $CH_3$ | $CH_3$ | 127-128 |
| 156 | $ClCH_2-CH_2-CH_2$ | $C_2H_5$ | 90-92 | $ClCH_2-CH_2-CH_2$ | $C_2H_5$ | $CH_3$ | 134 |
| 157 | $ClCH_2-CH_2-CH_2$ | $C_3H_7$ | 71-73 | $ClCH_2-CH_2-CH_2$ | $C_3H_7$ | $CH_3$ | 135 |
| 158 | $ClCH_2-CH_2-CH_2$ | H | 74-75 | $ClCH_2-CH_2-CH_2$ | H | $CH_3$ | 126 |
| 159 | $ClCH=CH-CH_2$ | $CH_2OCH_3$ |  | $ClCH=CH-CH_2$ | $CH_2OCH_3$ | $CH_3$ |  |
| 160 | $Cl_2C=CHCH_2$ | H |  | $Cl_2C=CH-CH_2$ | H | $CH_3$ |  |
| 161 | $Cl_2C=CHCH_2$ | $CH_3$ |  | $Cl_2C=CH-CH_2$ | $CH_3$ | $CH_3$ |  |
| 162 | $Cl_2C=CHCH_2$ | $C_2H_5$ |  | $Cl_2C=CH-CH_2$ | $C_2H_5$ | $CH_3$ |  |
| 163 | $Cl_2C=CHCH_2$ | $C_3H_7$ |  | $Cl_2C=CH-CH_2$ | $C_3H_7$ | $CH_3$ |  |
| 164 | $Cl_2C=CHCH_2$ | $CH_2OCH_3$ |  | $Cl_2C=CH-CH_2$ | $CH_2OCH_3$ | $CH_3$ |  |
| 165 | $ClCH=CCl-CH_2$ | H |  | $ClCH=CCl-CH_2$ | H | $CH_3$ |  |
| 166 | $ClCH=CCl-CH_2$ | $CH_3$ |  | $ClCH=CCl-CH_2$ | $CH_3$ | $CH_3$ |  |
| 167 | $ClCH=CCl-CH_2$ | $C_2H_5$ |  | $ClCH=CCl-CH_2$ | $C_2H_5$ | $CH_3$ |  |
| 168 | $ClCH=CCl-CH_2$ | $C_3H_7$ |  | $ClCH=CCl-CH_2$ | $C_3H_7$ | $CH_3$ |  |
| 169 | $ClCH=CCl-CH_2$ | $CH_2OCH_3$ |  | $ClCH=CCl-CH_2$ | $CH_2OCH_3$ | $CH_3$ |  |
| 170 | $H_3C-CCl=CH-CH_2$ | H |  | $H_3C-CCl=CH-CH_2$ | H | $CH_3$ |  |
| 171 | $H_3C-CCl=CH-CH_2$ | $CH_3$ |  | $H_3C-CCl=CH-CH_2$ | $CH_3$ | $CH_3$ |  |
| 172 | $H_3C-CCl=CH-CH_2$ | $C_2H_5$ |  | $H_3C-CCl=CH-CH_2$ | $C_2H_5$ | $CH_3$ |  |
| 173 | $H_3C-CCl=CH-CH_2$ | $C_3H_7$ |  | $H_3C-CCl=CH-CH_2$ | $C_3H_7$ | $CH_3$ |  |
| 174 | $H_3C-CCl=CH-CH_2$ | $CH_2OCH_3$ |  | $H_3C-CCl=CH-CH_2$ | $CH_2OCH_3$ | $CH_3$ |  |
| 175 | $FHC=CH-CH_2$ | H |  | $FHC=CH-CH_2$ | H | $CH_3$ |  |
| 176 | $FHC=CH-CH_2$ | $CH_3$ |  | $FHC=CH-CH_2$ | $CH_3$ | $CH_3$ |  |
| 177 | $FHC=CH-CH_2$ | $C_2H_5$ |  | $FHC=CH-CH_2$ | $C_2H_5$ | $CH_3$ |  |
| 178 | $FHC=CH-CH_2$ | $C_3H_7$ |  | $FHC=CH-CH_2$ | $C_3H_7$ | $CH_3$ |  |
| 179 | $FHC=CH-CH_2$ | $CH_2OCH_3$ |  | $FHC=CH-CH_2$ | $CH_2OCH_3$ | $CH_3$ |  |
| 180 | $C_3H_7$ | $CH_2-N(CH_3)_2$ |  | $C_3H_7$ | $CH_2-N(CH_3)_2$ | $CH_3$ |  |
| 181 | $C_3H_7$ | $CH_2-N(C_2H_5)_2$ |  | $C_3H_7$ | $CH_2-N(C_2H_5)_2$ | $CH_3$ |  |

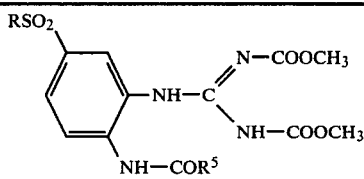

| Example No. | R | R⁵ |
|---|---|---|
| 229 | $C_3H_7$ | H |
| 230 | $C_3H_7$ | $CH_3$ |
| 231 | $C_3H_7$ | $C_3H_7$ |
| 232 | $C_3H_7$ | $C_4H_9$ |
| 233 | $C_3H_7$ | $C_5H_{11}$ |
| 234 | $C_3H_7$ | $CH_2OCH_3$ |
| 235 | $C_3H_7$ | $CH_2-N\begin{bmatrix}\end{bmatrix}$ |
| 236 | $C_4H_9$ | H |
| 237 | $C_4H_9$ | $CH_3$ |
| 238 | $C_4H_9$ | $C_2H_5$ |
| 239 | $C_4H_9$ | $C_3H_7$ |
| 240 | $C_4H_9$ | $C_4H_9$ |
| 241 | $C_4H_9$ | $CH_2OCH_3$ |
| 242 | $ClCH=CH-CH_2$ | H |
| 243 | $ClCH=CH-CH_2$ | $CH_3$ |
| 244 | $ClCH=CH-CH_2$ | $C_2H_5$ |
| 245 | $ClCH=CH-CH_2$ | $C_3H_7$ |
| 246 | $ClCH=CH-CH_2$ | $C_4H_9$ |
| 247 | $ClCH=CH-CH_2$ | $CH_2OCH_3$ |
| 248 | $NC-CH_2-CH_2$ | H |
| 249 | $NC-CH_2-CH_2$ | $CH_3$ |
| 250 | $NC-CH_2-CH_2$ | $C_2H_5$ |
| 251 | $NC-CH_2-CH_2$ | $C_3H_7$ |
| 252 | $NC-CH_2-CH_2$ | $C_4H_9$ |
| 253 | $NC-CH_2-CH_2$ | $CH_2OCH_4$ |
| 254 | $NC-CH_2-CH_2-CH_2$ | H |
| 255 | $NC-CH_2-CH_2-CH_2$ | $CH_3$ |
| 256 | $NC-CH_2-CH_2-CH_2$ | $C_2H_5$ |
| 257 | $NC-CH_2-CH_2-CH_2$ | $C_3H_7$ |
| 258 | $NC-CH_2-CH_2-CH_2$ | $C_4H_9$ |
| 259 | $NC-CH_2-CH_2-CH_2$ | $CH_2OCH_3$ |
| 260 | $H_3CO-CH_2-CH_2$ | H |
| 261 | $H_3CO-CH_2-CH_2$ | $CH_3$ |
| 262 | $H_3CO-CH_2-CH_2$ | $C_2H_5$ |
| 263 | $H_3CO-CH_2-CH_2$ | $C_3H_7$ |
| 264 | $H_3CO-CH_2-CH_2$ | $C_4H_9$ |
| 265 | $H_3CO-CH_2-CH_2$ | $CH_2OCH_3$ |
| 266 | $H_3CO-CH_2-CH_2-CH_2$ | H |
| 267 | $H_3CO-CH_2-CH_2-CH_2$ | $CH_3$ |
| 268 | $H_3CO-CH_2-CH_2-CH_2$ | $C_2H_5$ |
| 269 | $H_3CO-CH_2-CH_2-CH_2$ | $C_3H_7$ |
| 270 | $H_3CO-CH_2-CH_2-CH_2$ | $C_4H_9$ |
| 271 | $H_3CO-CH_2-CH_2-CH_2$ | $CH_2OCH_3$ |

EXAMPLE 272

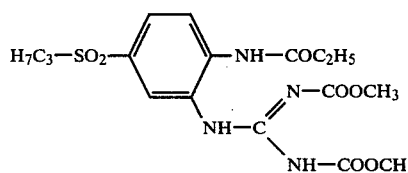

9.9 g of N-(2-propionylamino-propylthio-phenyl)-N,N''-bis-methoxycarbonyl-guanidine (Example 101) are dissolved in 200 ml of acetic anhydride. 25.8 ml of hydrogen peroxide (30% strength) are added, the mixture is stirred for 4 hours at 20° C. and concentrated in vacuo and the residue is recrystallised from ethyl acetate.

Yield: 7.37 g, Fp. 152° C. u. Z.

EXAMPLES 273 TO 315

In each of these Examples, a sulphoxide of the following general formula is obtained by oxidising the corresponding thioether in an analogous procedure to Example 272:

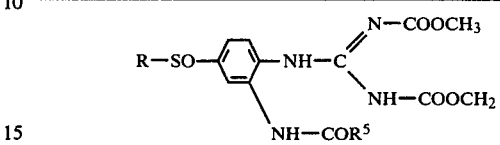

| Example No. | R | R⁵ |
|---|---|---|
| 273 | $C_3H_7$ | H |
| 274 | $C_3H_7$ | $CH_3$ |
| 275 | $C_3H_7$ | $C_3H_7$ |
| 276 | $C_3H_7$ | $C_4H_9$ |
| 277 | $C_3H_7$ | $C_5H_{11}$ |
| 278 | $C_3H_7$ | $CH_2OCH_3$ |
| 279 | $C_3H_7$ | $CH_2-N\begin{bmatrix}\end{bmatrix}$ |
| 280 | $C_4H_9$ | H |
| 281 | $C_4H_9$ | $CH_3$ |
| 282 | $C_4H_9$ | $C_2H_5$ |
| 283 | $C_4H_9$ | $C_3H_7$ |
| 284 | $C_4H_9$ | $C_4H_9$ |
| 285 | $C_4H_9$ | $CH_2OCH_3$ |
| 286 | $ClCH=CH-CH_2$ | H |
| 287 | $ClCH=CH-CH_2$ | $CH_3$ |
| 288 | $ClCH=CH-CH_2$ | $C_2H_5$ |
| 289 | $ClCH=CH-CH_2$ | $C_3H_7$ |
| 290 | $ClCH=CH-CH_2$ | $C_4H_9$ |
| 291 | $ClCH=CH-CH_2$ | $CH_2OCH_3$ |
| 292 | $NC-CH_2-CH_2$ | H |
| 293 | $NC-CH_2-CH_2$ | $CH_3$ |
| 294 | $NC-CH_2-CH_2$ | $C_4H_9$ |
| 295 | $NC-CH_2-CH_2$ | $C_3H_7$ |
| 296 | $NC-CH_2-CH_2$ | $C_4H_9$ |
| 297 | $NC-CH_2-CH_2$ | $CH_2OCH_3$ |
| 298 | $NC-CH_2-CH_2-CH_2$ | H |
| 299 | $NC-CH_2-CH_2-CH_2$ | $CH_3$ |
| 300 | $NC-CH_2-CH_2-CH_2$ | $C_2H_5$ |
| 301 | $NC-CH_2-CH_2-CH_2$ | $C_3H_7$ |
| 302 | $NC-CH_2-CH_2-CH_2$ | $C_4H_9$ |
| 303 | $NC-CH_2-CH_2-CH_2$ | $CH_2OCH_3$ |
| 304 | $H_3CO-CH_2-CH_2$ | H |
| 305 | $H_3CO-CH_2-CH_2$ | $CH_3$ |
| 306 | $H_3CO-CH_2-CH_2$ | $C_2H_5$ |
| 307 | $H_3CO-CH_2-CH_2$ | $C_3H_7$ |
| 308 | $H_3CO-CH_2-CH_2$ | $C_4H_9$ |
| 309 | $H_3CO-CH_2-CH_2$ | $CH_2OCH_3$ |
| 310 | $H_3CO-CH_2-CH_2-CH_2$ | H |
| 311 | $H_3CO-CH_2-CH_2-CH_2$ | $CH_3$ |
| 312 | $H_3CO-CH_2-CH_2-CH_2$ | $C_2H_5$ |
| 313 | $H_3CO-CH_2-CH_2-CH_2$ | $C_3H_7$ |
| 314 | $H_3CO-CH_2-CH_2-CH_2$ | $C_4H_9$ |
| 315 | $H_3CO-CH_2-CH_2-CH_2$ | $CH_2OCH_3$ |

EXAMPLES 316 TO 358

In each of these Examples, a compound of the following general formula is obtained by oxidising the corresponding thioether in an analogous procedure to Example 272.

-continued

| | Starting materials | | | Substances prepared according to the invention | | |
|---|---|---|---|---|---|---|
| | 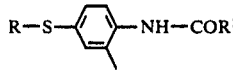 | | | 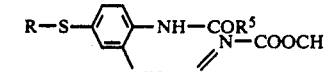 | | |
| Ex. No. | R | R⁵ | Melting point (°C.) | R | R⁵ | R⁴ | Melting point (°C.) |
| 182 | $C_3H_7$ |  | | $C_3H_7$ | 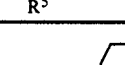 | $CH_3$ | |
| 183 | $C_3H_7$ | 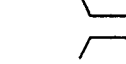 | | $C_3H_7$ |  | $CH_3$ | 97–98 |
| 184 | $C_3H_7$ | 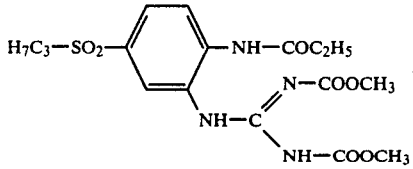 | | $C_3H_7$ | 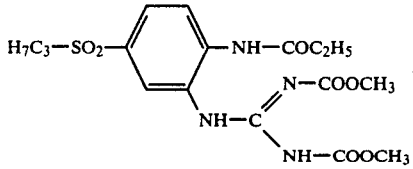 | $CH_3$ | |

EXAMPLE 185

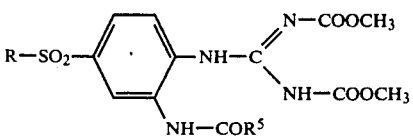

19.8 g of N-(2-proplonylamino-5-propylthio-phenyl)-N'-N''-bis-methoxycarbonyl-guanidine (Example 5) are dissolved in 650 ml of acetic anhydride. 42 g of hydrogen peroxide (30% strength) are added and the mixture is stirred overnight and evaporated in vacuo.

The residue crystallises (after triturating with a mixture of ethyl acetate and ether). The precipitate is filtered off and recrystallised and ethyl acetate. Yield: 22.2 g, Fp 165°–166° C. u. Z.

EXAMPLES 186 TO 228

In each of the Examples a sulphone of the following general formula is obtained by oxidising the corresponding thioether in an analogous procedure to Example 185.

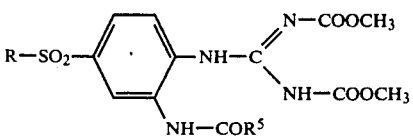

| Example No. | R | R⁵ |
|---|---|---|
| 186 | $C_3H_7$ | H |
| 187 | $C_3H_7$ | $CH_3$ |
| 188 | $C_3H_7$ | $C_3H_7$ |
| 189 | $C_3H_7$ | $C_4H_9$ |
| 190 | $C_3H_7$ | $C_5H_{11}$ |
| 191 | $C_3H_7$ | $CH_2OCH_3$ |
| 192 | $C_3H_7$ | 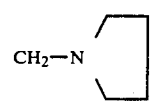 |
| 193 | $C_4H_9$ | H |

-continued

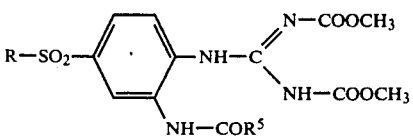

| Example No. | R | R⁵ |
|---|---|---|
| 194 | $C_4H_9$ | $CH_3$ |
| 195 | $C_4H_9$ | $C_2H_5$ |
| 196 | $C_4H_9$ | $C_3H_7$ |
| 197 | $C_4H_9$ | $C_4H_9$ |
| 198 | $C_4H_9$ | $CH_2OCH_3$ |
| 199 | $ClCH=CH-CH_2$ | H |
| 200 | $ClCH=CH-CH_2$ | $CH_3$ |
| 201 | $ClCH=CH-CH_2$ | $C_2H_5$ |
| 202 | $ClCH=CH-CH_2$ | $C_3H_7$ |
| 203 | $ClCH=CH-CH_2$ | $C_4H_9$ |
| 204 | $ClCH=CH-CH_2$ | $CH_2OCH_3$ |
| 205 | $NC-CH_2-CH_2$ | H |
| 206 | $NC-CH_2-CH_2$ | $CH_3$ |
| 207 | $NC-CH_2-CH_2$ | $C_2H_5$ |
| 208 | $NC-CH_2-CH_2$ | $C_3H_7$ |
| 209 | $NC-CH_2-CH_2$ | $C_4H_9$ |
| 210 | $NC-CH_2-CH_2$ | $CH_2OCH_3$ |
| 211 | $NC-CH_2-CH_2-CH_2$ | H |
| 212 | $NC-CH_2-CH_2-CH_2$ | $CH_3$ |
| 213 | $NC-CH_2-CH_2-CH_2$ | $C_2H_5$ |
| 214 | $NC-CH_2-CH_2-CH_2$ | $C_3H_7$ |
| 215 | $NC-CH_2-CH_2-CH_2$ | $C_4H_9$ |
| 216 | $NC-CH_2-CH_2-CH_2$ | $CH_2OCH_3$ |
| 217 | $H_3CO-CH_2-CH_2$ | H |
| 218 | $H_3CO-CH_2-CH_2$ | $CH_3$ |
| 219 | $H_3CO-CH_2-CH_2$ | $C_2H_5$ |
| 220 | $H_3CO-CH_2-CH_2$ | $C_3H_7$ |
| 221 | $H_3CO-CH_2-CH_2$ | $C_4H_9$ |
| 222 | $H_3CO-CH_2-CH_2$ | $CH_2OCH_3$ |
| 223 | $H_3CO-CH_2-CH_2-CH_2$ | H |
| 224 | $H_3CO-CH_2-CH_2-CH_2$ | $CH_3$ |
| 225 | $H_3CO-CH_2-CH_2-CH_2$ | $C_2H_5$ |
| 226 | $H_3CO-CH_2-CH_2-CH_2$ | $C_3H_7$ |
| 227 | $H_3CO-CH_2-CH_2-CH_2$ | $C_4H_9$ |
| 228 | $H_3CO-CH_2-CH_2-CH_2$ | $CH_2OCH_3$ |

EXAMPLES 229 TO 272

In each of these examples, a sulphone of the following general formula is obtained by oxidising the corresponding thioether in an analogous procedure to Example 185:

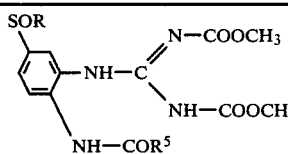

| Example No. | R | R⁵ |
|---|---|---|
| 316 | $C_3H_7$ | H |
| 317 | $C_3H_7$ | $CH_3$ |
| 318 | $C_3H_7$ | $C_3H_7$ |
| 319 | $C_3H_7$ | $C_4H_9$ |
| 320 | $C_3H_7$ | $C_3H_{11}$ |
| 321 | $C_3H_7$ | $CH_2OCH_3$ |
| 322 | $C_3H_7$ | $CH_2-N\begin{pmatrix}\end{pmatrix}$ |
| 323 | $C_4H_9$ | H |
| 324 | $C_4H_9$ | $CH_3$ |
| 325 | $C_4H_9$ | $C_2H_5$ |
| 326 | $C_4H_9$ | $C_3H_7$ |
| 327 | $C_4H_9$ | $C_4H_9$ |
| 328 | $C_4H_9$ | $CH_2OCH_3$ |
| 329 | $ClCH=CH-CH_2$ | H |
| 330 | $ClCH=CH-CH_2$ | $CH_3$ |
| 331 | $ClCH=CH-CH_2$ | $C_2H_5$ |
| 332 | $ClCH=CH-CH_2$ | $C_3H_7$ |
| 333 | $ClCH=CH-CH_2$ | $C_4H_9$ |
| 334 | $ClCH=CH-CH_2$ | $CH_2OCH_3$ |
| 335 | $NC-CH_2-CH_2$ | H |
| 336 | $NC-CH_2-CH_2$ | $CH_3$ |
| 337 | $NC-CH_2-CH_2$ | $C_2H_5$ |
| 338 | $NC-CH_2-CH_2$ | $C_3H_7$ |
| 339 | $NC-CH_2-CH_2$ | $C_4H_9$ |
| 340 | $NC-CH_2-CH_2$ | $CH_2OCH_3$ |
| 341 | $NC-CH_2-CH_2-CH_2$ | H |
| 342 | $NC-CH_2-CH_2-CH_2$ | $CH_3$ |
| 343 | $NC-CH_2-CH_2-CH_2$ | $C_2H_5$ |
| 344 | $NC-CH_2-CH_2-CH_2$ | $C_3H_7$ |
| 345 | $NC-CH_2-CH_2-CH_2$ | $C_4H_9$ |
| 346 | $NC-CH_2-CH_2-CH_2$ | $CH_2OCH_3$ |
| 347 | $H_3CO-CH_2-CH_2$ | H |
| 348 | $H_3CO-CH_2-CH_2$ | $CH_3$ |
| 349 | $H_3CO-CH_2-CH_2$ | $C_2H_5$ |
| 350 | $H_3CO-CH_2-CH_2$ | $C_3H_7$ |
| 351 | $H_3CO-CH_2-CH_2$ | $C_4H_9$ |
| 352 | $H_3CO-CH_2-CH_2$ | $CH_2OCH_3$ |
| 353 | $H_3CO-CH_2-CH_2-CH_2$ | H |
| 354 | $H_3CO-CH_2-CH_2-CH_2$ | $CH_3$ |
| 355 | $H_3CO-CH_2-CH_2-CH_2$ | $C_2H_5$ |
| 356 | $H_3CO-CH_2-CH_2-CH_2$ | $C_3H_7$ |
| 357 | $H_3CO-CH_2-CH_2-CH_2$ | $C_4H_9$ |
| 358 | $H_3CO-CH_2-CH_2-CH_2$ | $CH_2OCH_3$ |

EXAMPLES FOR THE MANUFACTURE OF COMPOSITIONS

Example C 1

A formulation having the following composition is prepared:

| | |
|---|---|
| (A) N-(2-butyramido-4-propylthio-phenyl)-N'-N''-bis-methoxy-carbonyl-guanidine | 50,0% |
| (B) Lecithin | 1,5% |
| (C) Polyoxyethylenesorbitantrioleate | 2,0% |
| (D) Polyethyleneglycol-laurylether (stabilizer) | 2,0% |
| (E) Mineral Oil | 43,5% |

This formulation is prepared by mixing the components B to E and adding component A by stirring until a uniform dispersion is completed.

Example C 2

A suspension having the following formulation is prepared:

| | |
|---|---|
| (A) The formulation of example C 1 | 10 g |
| (B) Polyoxyethylenesorbitantrioleate | 4 g |
| (C) Polyethyleneglycol-laurylether (stabilizer) | 4 g |
| (D) Oleum Arachidoni | 70 g |

This formulation is prepared by mixing and stirring the components until it is a uniform dispersion is completed.

Example C 3

A formulation having the following composition is prepared:

| | |
|---|---|
| (A) N-(2-butyramido-4-propylthio-phenyl)-N'-N''-bis-methoxy-carbonyl-guanidine | 30% |
| (B) Polyethylenglycol 6000 | 40% |
| (C) (Polyoxy(40)stearate) | 30% |

The components Polyethyleneglycol 6000 and Polyoxy(40)stearate are mixed at 50°-60° C. and then component 1 is added by stirring. The formulation is solidified by cooling and ground, without remelting of the polyethylene glycol, to a fine powder.

EXAMPLE C 4

A drenchpowder having the following composition is prepared:

| | |
|---|---|
| (A) The formulation of example C 3 | 15 g |
| (B) colloidal silica | 6 g |
| (C) Carboxymethylcellulose | 6 g |

The components are blended together until uniform and then are finely powdered.

EXAMPLE C 5

A suspension having the following formulation is prepared:

| | |
|---|---|
| (A) The formulation of example C 3 | 7,5 g |
| (B) citric acid, hydrous | 0,43 g |
| (C) sodium citrat | 0,67 g |
| (D) carboxymethylcellulose | 1,1 g |
| (E) colloidal silica | 1 g |
| (F) sorbic acid | 0,3 g |
| (G) purified water | to 100 ml |

The sorbic acid, citric acid and sodium citrate are added to 90 ml of water which has been heated to 80° C. The colloidal silica and carboxymethyl cellulose are then added, with stirring, until uniformly dispersed and fully hydrated. The mixture is cooled to 45° C. and the formulation of Example 3 is added, with stirring, until it is uniformly dispersed. The suspension is cooled to room temperature and the balance of the water is added.

EXAMPLE C 6

A formulation having the following composition is prepared:

(A) N-(2-Propionamido-4-propylthio-phenyl)-N'-N'-bis-

-continued

| | |
|---|---|
| methoxycarbonyl-guanidine | 50% |
| (B) Lecithin | 1,5% |
| (C) Polyoxyethylenesorbitantioleate | 2% |
| (D) Polyethyleneglycol-laurylether | 2% |
| (E) Mineral Oil | 43,5% |

This formulation is prepared by mixing the components 2–5 and adding with stirring the component 12 until a uniform dispersion is completed.

EXAMPLE C 7

A suspension having the following formulation is prepared:

| | |
|---|---|
| (A) The formulation of example C 6 | 10 g |
| (B) Polyoxyethylenesorbitantrioleate | 4 g |
| (C) Polyethyleneglycol-laurylether | 4 g |
| (D) Oleum Arachidoni | 70 g |

This formulation is prepared by mixing and stirring the components until a uniform dispersion is completed.

EXAMPLE C 8

A formulation having the following composition is prepared:

| | |
|---|---|
| (A) N(2-Propionamido-4-propylthio-phenyl)-N'-N''-bis-methoxy-carbonyl-guanidine | 30% |
| (B) Polyethylenglycol (6000) | 40% |
| (C) (Polyoxy(40)stearate) | 30% |

The components (B) and (C) are mixed at 50°–60° C. and then is component A is added by stirring. The formulation is solidified by cooling and ground, without remelting of the polyethylene glycol, to a fine powder.

EXAMPLE C 9

A drenchpowder having the following composition is prepared:

| | |
|---|---|
| (A) The formulation of example C 8 | 15 g |
| (B) colloidal silica | 6 g |
| (C) Carboxymethylcellulose | 6 g |

The components are blended together until uniform and then are finely powdered.

EXAMPLE C 10

A suspension having the following formulation is prepared:

| | |
|---|---|
| (A) The formulation of example C 8 | 7,5 g |
| (B) citric acid, hydrous | 0,43 g |
| (C) sodium citrat | 0,67 g |
| (D) carboxymethylcellulose | 1,1 g |
| (E) colloidal silica | 1 g |
| (F) sorbic acid | 0,3 g |
| (G) purified water | to 100 ml |

The sorbic acid, citric acid and sodium citrate are added to 90 ml of water which has been heated to 80° C. The colloidal silica and carboxymethyl cellulose are then added, with stirring, until uniformly dispersed and fully hydrated. The mixture is cooled to 45° C. and the formulation of Example 8 is added, with stirring, until it is uniformly dispersed. The suspension is cooled to room temperature and the balance of the water is added.

What is claimed is:

1. A substituted ophenyldiamine derivative of the formula

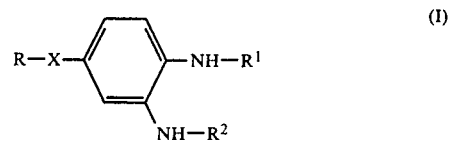

in which

X represents S, SO or $SO_2$,

R represents a straight chain or branched alkyl group of from 1 to 6 carbon atoms, or a straight chain or branched alkenyl or alkinyl group of from 2 to 6 carbon atoms, the alkyl, alkenyl or alkinyl group being unsubstituted or substituted by halogen, cyano, $(C_1-C_4)$-alkoxy or $(C_1-C_4)$-alkylthio;

$R^1$ and $R^2$ are different from one another and individually represent

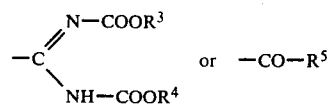

in which $R^3$ and $R^4$ represent straight chain or branched alkyl groups of from 1 to 6 carbon atoms, $R^5$ represents hydrogen, or a straight chain or branched alkyl group with 1 to 6 carbon atoms or a straight-chain or branched alkoxy group of from 1 to 6 carbon atoms, the alkyl or alkoxy group being unsubstituted or substituted by halogen, cyano, $(C_1-C_6)$-alkoxy, $(C_1-C_4)$-alkylmercapto, or by a radical of the formula

in which $R^6$ and $R^7$ are identical or different and each represents hydrogen, $(C_1-C_4)$-alkyl which is unsubstituted or substituted by $(C_1-C_4)$-alkoxy, trifluoromethyl or cyano, or in which the two radicals $R^6$ and $R^7$, together with the nitrogen atom to which they are attached, form a 5-, 6- or 7-membered pyrrolidinyl, piperidinyl, hexamethyleneiminyl, thiomorpholinyl, piperazinyl or N-methylaminomethyl ring or a salt thereof.

2. A compound of claim 1 wherein X represents S.

3. A compound of claim 1 wherein X represents SO.

4. A compound of claim 1 wherein X represents $SO_2$.

5. A compound of claim 1 in the form of a physiologically acceptable salt.

6. A pharmaceutical composition containing as an active ingredient an anthelmintically effective amount of a compound of claim 1 in admixture with a solid or liquefied gaseous diluent or in admixture with a liquid diluent other than a solvent of a molecular weight less than 200 except in the presence of a surface-active agent.

7. A pharmaceutical composition containing as an active ingredient an anthelmintically effective amount of a compound of claim 1 in the form of a sterile or isotonic aqueous solution.

8. A composition of claim 7 containing from 0.5 to 95% by weight of the said active ingredient.

9. A composition of claim 6 containing from 0.5 to 95% by weight of said active ingredient.

10. A medicament in dosage unit form comprising an anthelmintically effective amount of a compound of claim 1 and an inert pharmaceutical carrier.

11. A medicament of claim 10 in the form of tablets, pills, dragees, capsules, ampoules, or suppositories.

12. A method of combating helminthiases in a warmblooded animal which comprises administering to said animal an anthelmintically effective amount of a compound of claim 1 either alone or in admixture with a diluent or in the form of a medicament.

13. A method of claim 12 in which the active compound is administered in an amount of 0.1 to 50 mg per kg body weight per day.

14. A method according to claim 12 in which the active compound is administered orally or parenterally.

15. Compound having formula

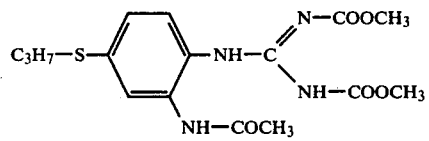

16. Compound having formula

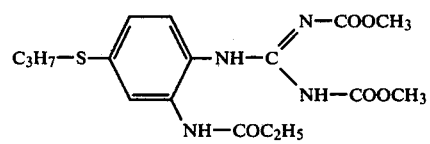

17. Compound having formula

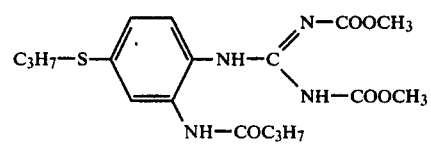

18. Compound having formula

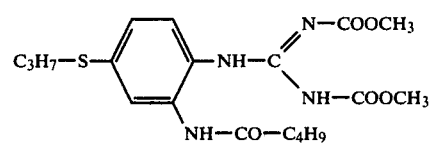

19. Compound having formula

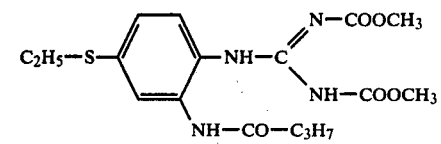

20. Compound having formula

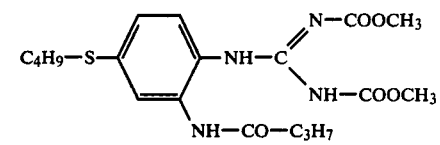

21. Compound having formula

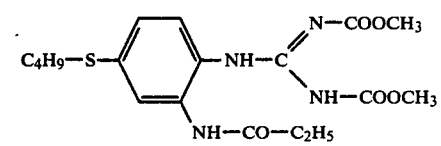

22. Compound having formula

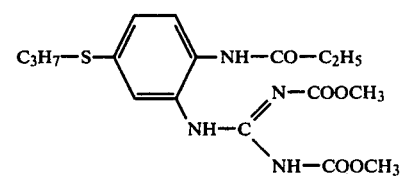

23. Compound having formula

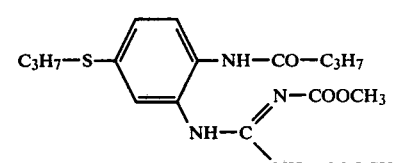

24. Compound having formula

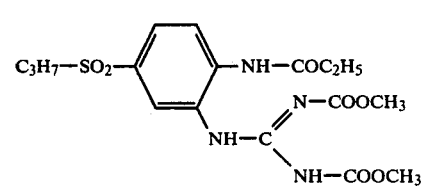

25. Compound having formula

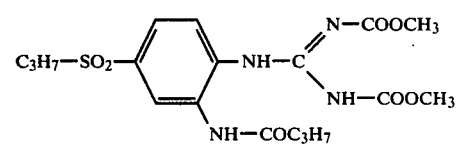

26. Compound having formula

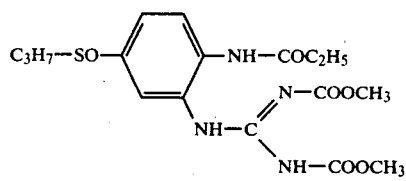
27. Compound having formula
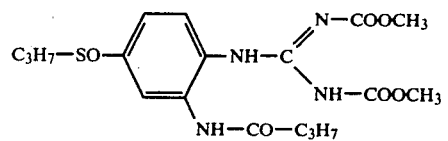
* * * * *